(12) United States Patent
Hsu et al.

(10) Patent No.: US 7,629,154 B2
(45) Date of Patent: Dec. 8, 2009

(54) DEINOCOCCUS N-ACYLAMINO ACID RACEMASE AND USE OF PREPARING L-AMINO ACID

(75) Inventors: Wen-Huei Hsu, Taichung (TW); Shih-Kuang Hsu, Taichung (TW)

(73) Assignee: National Chunghsing University, Taichung (TW)

( * ) Notice: Subject to any disclaimer, the term of this patent is extended or adjusted under 35 U.S.C. 154(b) by 108 days.

(21) Appl. No.: 11/316,818

(22) Filed: Dec. 27, 2005

(65) Prior Publication Data

US 2008/0003640 A1 Jan. 3, 2008

(30) Foreign Application Priority Data

Feb. 18, 2005 (TW) .............................. 94104909 A

(51) Int. Cl.
- C12P 13/04 (2006.01)
- C12P 19/34 (2006.01)
- C07H 21/00 (2006.01)

(52) U.S. Cl. ...................... 435/106; 435/91.1; 536/25.3
(58) Field of Classification Search ...................... None
See application file for complete search history.

*Primary Examiner*—David J Steadman
*Assistant Examiner*—Alexander D Kim
(74) *Attorney, Agent, or Firm*—Bacon & Thomas, PLLC

(57) ABSTRACT

The present invention relates to a novel thermostable N-acylamino acid racemase (NAAAR) isolated from *Deinococcus radiodurans* NCHU1003, the coding sequence and the preparation thereof. The present invention also discloses the process for preparing highly optically pure L-amino acids, such as L-homophenylalanine (L-HPA) and the derivatives thereof, from N-protected amino acid by using the novel NAAAR combined with L-N-carbamoylase.

20 Claims, 3 Drawing Sheets

DEINOCOCCUS N-ACYLAMINO ACID RACEMASE AND USE OF PREPARING L-AMINO ACID

BACKGROUND OF THE INVENTION

1. Field of the Invention

The present invention relates to the novel thermostable N-acylamino acid racemase (NAAAR) from *Deinococcus radiodurans* NCHU1003, the coding sequence and the preparation thereof. The present invention also relates to an improved process for the preparation of optically active L-amino acid, such as L-homophenylalanine (L-HPA) and the derivatives thereof, from their corresponding N-protected amino acid by using the novel NAAAR combined with L-N-carbamoylase.

2. Background of the Invention

Optically active amino acids, including the L- and D-form amino acids, have been widely used in the industry of food, feedstuff, pharmaceutical synthesis and agricultural chemistry as preparative materials. However, different type of optically active isomers may exhibit totally different biological activities. For instance, some optically active isomer with certain configuration possesses excellent biological activities, but the other isomer does not have such biological activities. When these two isomers are present at the same time, they not only reduce the biological activities but also further inhibit the existing biological activities. For that reason, it is important to find the way for producing enamtiomeric form of amino acid in the pharmaceutical industry.

In the prior art of optically active amino acid preparation, it was performed with chemical synthesis. However, the process of organic synthesis often results in involved environmental pollution and has high cost in isolation and purification. Accordingly, there are lots of limitations in large-scale production. Asymmetric hydrogenation and enzyme-catalyzed reaction were therefore developed for producing high purity optically active amino acids and derivatives thereof. Frank J. Villani Jr et al (1998) isolated the racemic amino acids with tartaric acid and salicylaldehyde, which obtains a product of 32% yield, with e.e. (enantiomeric excess) value of 94%. According to the literatures, there are many bioconversion methods for preparing L-amino acids, but most of such methods still remain nearly 50% of D-formed materials. Based on that the advantages of substrate-specificity, sterechemical selectivity and the like, enzyme-catalyzed process are used in the racemation of amino acid for the production of highly pure optically active amino acids. Non-naturally occurred L-amino acids can be produced by using D,L-5-monosubstituted acetolactams as substrates and *Arthrobacter* sp. DSM3745 as biocatalyst (Syldatk et al 1992). Similar methods have been applied to other microorganisms, such as *Pseudomonas, Achromobacter, Serratia, Aspergillus* and so on. Tseng et al (1991) used an enzyme-catalyzed specific stereoselective acetylation of (R)-2-hydroxyl-4-phenylbutyronitrile to produce L-amino acids, but this method required more than 12 days to complete the reaction.

Chen et al (1999) used aspartic acid and 2-oxo-4-phenylbutyric acid as substrates and the enzyme tyrosine aminotransferase to perform an equilibrium shift controlled enzymatic reaction for the production of pure L-HPA. Zhao et al use a commercialized protease—alcalase to produce L-HPA in large-scale in which an e.e. value of 98% can be obtained. This method used N-protected amino acid as substrate, and only L-form N-protected amino acid could be hydrolysed, so that can accomplish the isolation of desired products. However, such enzyme-catalyzed reaction is very complicate, for that the substrate must be protected previously and the protective group should be removed after the enzyme-catalyzed reaction. An alternative enzyme-catalyzed method are preformed by using L-amino acid acylase, which specifically acts on N-protected amino acid, to convert N-protected amino acid racemic mixture to L- or D-formed amino acid (EP99118844 and JP11318442A). Thereafter, the remaining D-formed N-protected amino acid may be converted to L-formed N-protected amino acid by physical or chemical racemation (as described in JP656775A). The difficulty of such process was the reaction must be repeated again and the product and reactants must be isolated after each reaction. Moreover, reaction temperature and pH are increased to racemize the remaining D-formed N-protected amino acid. L-Amino acid may also be produced by using amino acid acyl transferase, which specifically acts on the N-protected amino acid, and further racemation to convert remaining D-formed N-protected amino acid to L-form amino acid (EP99118844.2; and Bommarius A. S. et al, Tetrahedron Asymmetry, 1997, 8:3197-3200).

The N-acylamino acid racemase from actinomycetes was firstly discovered by Takahashi (1991). This enzyme only performs racemation on N-protected amino acids and not on non-protected amino acids. Only few NAAARs were reported to which most of them are from actinomycetes, such as *Streptomyces atratus* Y-53 (Tokuyama et al, *Appl. Microbiol. Biotechnol.* 1994, 40: 835-840; and *Amycolatopis* sp. TS-1-60, Tokuyama et al, *Appl. Microbiol. Biotechnol.* 1995a, 42: 853-859). The NAAAR from *Amycolatopis* sp. TS-1-60 can maintains its activity at 55° C. for about 30 min, but the presence of D, L-amino acid acyl transferase in *Amycolatopis* can interfere the optical purity of methionine, thus limits its application.

L-homophenylalanine (L-HPA) is an optically active unnatured amino acid which can be useful as intermediates for the synthesis of many antihypertension drugs, ACE inhibitors. So far the high purity of L-HPA and derivative thereof is produced by chemical resolution or asymmetric hydrogenation (U.S. Pat. No. 5,981,794 and EP00902011A1). However, the previous methods must be carried out in a condition of high temperature and strong base, which exhibits the problems in expense, safety and environmental conservation and could not achieve best ee value and yield. The process of present invention is an enzyme catalytic method, so its reaction condition may avoid the disadvantages occurred in the chemical methods.

The production of L-HPA by enzymetic processes has been focused on amino transferase using L-aspartic acid or L-glutamic acid as the amino donor, and 2-oxo-4-phenyl butyric acid as the amino acceptor to obtain high purity L-PHA. Syldatk, C et al (1992) used the hydantoinase capable of catalying D, L-5-monosubstituted hydantoins in combination with D-N-carbamoylase or L-N-carbamoylase to produce novel D- or L-formed amino acids. The hydantoinase process had been applied in the production of L-PHA (Lo & Hsu 2003). In this process the hydantoinase is isolated from *B. agri*, since the substrate specificity of this hydantoinase is favor D-form homophenylalaninyl hydantoin (D-HPAH), a large amount of intermediate (D-NCaHPA) is formed during the process and therefore disadvantaged to the biosynthesis of L-HPA.

The present invention provides an enzymetic process for producing L-HPA with high optical purity by using a novel thermostable N-acylamino acid racemase (NAAAR) from *Deinococcus radiodurans* NCHU1003 and a carbamoylase from *Deinococcus* sp.

SUMMARY OF THE INVENTION

In one aspect, the present provides a novel thermostable N-acylamino acid racemase (NAAAR) from *Deinococcus radiodurans* NCHU1003, and the coding sequence thereof. The present NAAAR possesses excellent thermostability at 55° C. with half-life of about 15 days.

In a preferable embodiment of the invention, the NAAAR coding sequence is cloned in an appropriate expression vector, which is, for example, transformed into *E. coli* host cell for readily preparing the NAAAR.

In another aspect, the present provides a method for preparing L-HPA from the N-protected amino acid by using the present NAAAR combined with L-carbamoylase.

In an embodiment of the invention, the conversion of N-carbamoyl protected HPA to L-HPA is carried out by the isolated NAAAR and L-carbamoylase. In another embodiment of the invention, the NAAAR and L-carbamoylase are expressed in an *E. coli* host cell, and L-HPA is produced by the whole cell preparation from the N-protected starting material.

DETAILED DESCRIPTION OF THE PREFERRED EMBODIMENTS

Figure 1:
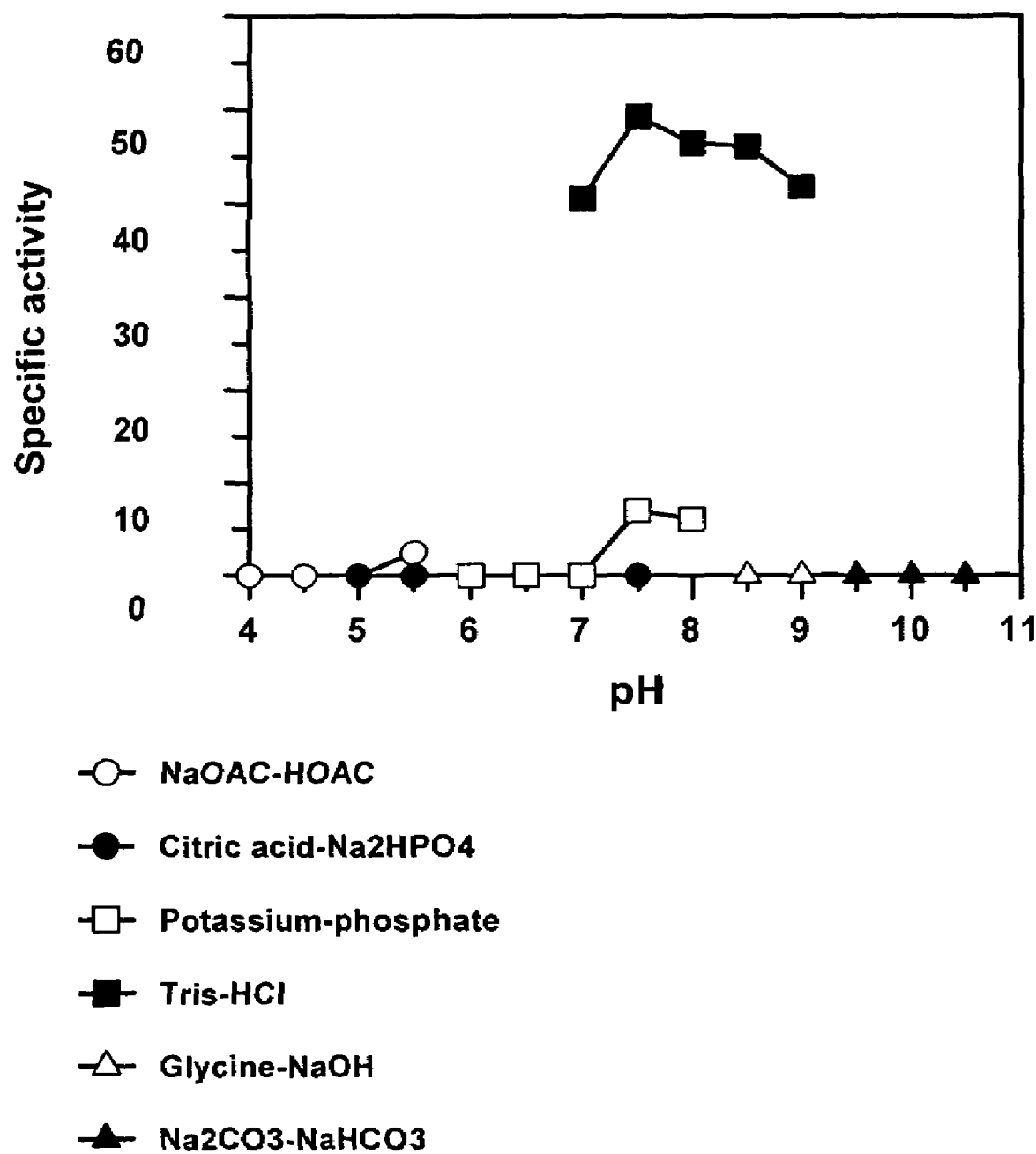
FIG. 1 shows the effects of pH on the catalytic activity of the present N-acylamino acid racemase.

N-acylamino acid racemase (NAAAR) specifically acts on racemic N-protected amino acids and catalyzes the conversion of racemic N-protected amino acid to optically active N-protected amino acid. The present invention is characterized by first cloning the encoding sequence of NAAAR from *Deinococcus radiodurans* NCHU1003 genomic DNA. By using genetic engineering technique, the NAAAR gene is expressed in host cells such as *E. coli* cells and ready for preparing L-HPA in isolated form or in whole cell preparation combined with L-carbamoylase. The amino acid sequence of the present *Deinococcus radiodurans* NCHU1003 NAAAR and nucleotide encoding sequence are listed in SEQ ID Nos. 1 and 2.

The present invention also provides the recombinant DNA or RNA molecules comprising the NAAAR, which including and not limiting to phages, plasmids, phagemids, cosmids, YACs (yeast artificial fragmentation), BACs (bacteria artificial fragmentation) and the like. The methods for preparing such molecules are well known in the art, such as described in Sambrook et al, Molecular Cloning: A Laboratory Manual, 2dn Ed., New York, Cold Spring Harbor Express, 1989.

In a preferable embodiment of the invention, the recombinant DNA technology is provided to produce a fusion protein of L-N-carbamoylase with the present NAAAR from *Deinococcus RADIO DURANS* NCHU1003. The fusion construct is produced at DNA level by incorporating particular restriction sites for the insertion of desired DNA fragments into a proper expression vector, and is used in a heterologous expression system to express the desired fusion protein.

As used herein, the term "vector" refers to the plasmid which carrying DNA coding the desired protein. The exemplary vectors used in the present invention include, but not limited to, expression vector pQE30.

The gene encoding the protein is operatively linked to a gene expression sequence that directs the expression of the protein within a prokaryotic cell such as *E. coli*. The "gene expression sequence" is any regulatory nucleotide sequence, such as a promoter sequence or promoter-enhancer combination, which facilitates the efficient transcription and translation of the protein to which it is operatively linked. The promoters useful as gene expression sequences of the invention also include inducible promoters. Inducible promoters are expressed in the presence of an inducing agent, which is known to those of ordinary skill in the art.

The L-N-carbamoylase coding gene is obtained from any appropriate source by polymerase chain reaction (PCR) method. In order to facilitate the subsequent cloning steps, it is preferable to design the primers with unique restriction sites. Similarly, The *Deinococcus radiodurans* NCHU1003 NAAAR coding sequence may be provided by PCR method using the primers with unique restriction sites for the further cloning into suitable expression vector and/or fusion with the L-N-carbamoylase gene.

The present process for preparing L-HPA by using the NAAAR combined with L-N-carbamoylase may be carried in a condition that the NAAAR and L-N-carbamoylase is added respectively. In such cases, these two enzymes may be added to the reaction mixture containing substrate simultaneously or sequentially. In another way, the enzymes may be immobilized on a support (or supports) and react with the substrate in suitable conditions. The supports useful in the present invention includes, for example, resins, beads, films, surface of microtitration plates and the like.

Alternatively, the method of present invention is preformed in the whole cell preparation of transformed cells which expressing the NAAAR and L-N-carbamoylase genes cloned in the same or individual expression vector. In one embodiment, the whole *E. coli* cells which have been transformed with a plasmid comprising NAAAR and L-N-carbamoylase encoding sequences is used in the conversion of N-carbamoyl protected phenylalanine to produce highly pure L-HPA.

EXAMPLE

The present invention is further illustrated by the following examples, which however, are not to be construed as limiting the scope of protection.

Example 1

Cloning and Expression of NAAAR Gene

The NAAAR gene was amplified by the polymerase chain reaction using primers DRI-01 (5'-CGCGGATCCATGGCG-CATACTGGCCGTATGT-3', SEQ ID NO: 3), containing BamHI restriction site, and DRI-02 (5'-CCCAAGCTTTCACGCCCGGTGTTCCTCCT-3', SEQ ID NO: 4), containing HindIII restriction site, and *Deinococcus radiodurans* NCHU1003 chromosomal DNA as template and cloned into a expression vector pQE30 resultant plasmid, pQE-naaar, was then transformed into host cell *E. coli* JM109 by $CaCl_2$ method. From the sequencing data of isolated NAAAR gene, SEQ ID NO: 2, the identity of the present NAAAR with known *Deinococcus radiodurans* strain is 96%.

The *E. coli* host cells harboring pQE-naaar were cultured with shaking at 37° C. overnight in a 500-mL flask containing 100 ml of LB medium with appropriate concentration of ampicillin. After 4 h incubation at 37° C. ($OD_{600}$ about 6 to 8), isopropyl-β-D-thiogalactoside was added to a final concentration of 0.1 to 1 mM, and further cultured at 30° C. for 6 h to induce the expression of NAAAR gene. The culture of induced bacteria was centrifuged at 12,000 rpm for 10 min.

The bacteria culture induced as described above was centrifuged at 3,000 rpm for 15 min, and the supernatant was discarded. The collected bacteria were washed with 50 mM Tris-HCl (pH 8.0), and disrupted by ultra-sonicator. The cell lysate was then centrifuged at 13,500 rpm at 4° C. for 20 min. The supernatant was filtrated through 0.45 μm membranes, and the NAAAR proteins were purified by column chromatography using Ni-NTA resin (Qiagene).

The enzymatic activity was determined by measuring the production profile of conversion product at 215 nm via HPLC method as described by Tokuyama et al (1994). The reaction buffer containing 10 mM substrate, 0.5 mM $CoCl_2$ and appropriate amount of the enzyme in 50 mM Tris-HCl buffer (pH 8.0) was incubated at 50° C. for 30 min, and the reaction was terminated by placing in boiling water for 5 min. The enzymatic activity was then measured by a Chiral-HPLC method. The $K_m$ values (mM) were determined from the original velocity data and the changes in NAc-D-HPA or NAc-D-HPA concentration. The unit NAAAR activity was defined as the enzyme amount required for catalysing 1 μmole of product formation under used condition. As described in the following Table 1, the specific activity of NAAAR for substrate N-carbamoyl-D-HPA was 1.31 U/mg, see Table 1.

TABLE 1

Substrate selectivity of present N-acylamino acid racemase

| Substrate | Specific activity (U/mg) | Relative activity (%)[a] |
| --- | --- | --- |
| N-acetyl-D-HPA | 9.17 | 143.28 |
| N-acetyl-L-HPA | 11.97 | 187.03 |
| N-acetyl-D-Met | 6.40 | 100 |
| N-acetyl-L-Met | 8.04 | 125.63 |
| N-acetyl-D-Phe | 1.98 | 30.94 |
| N-acetyl-L-Phe | 1.55 | 24.22 |
| N-acetyl-L-Gln | 0.93 | 14.53 |
| N-acetyl-L-Leu | 0.45 | 7.03 |
| N-acetyl-L-Trp | 0.87 | 13.13 |
| N-chloroacetyl-L-Phe | 1.16 | 18.13 |
| N-carbamoyl-D-HPA | 1.31 | 20.46 |
| N-carbamoyl-L-HPA | 1.91 | 29.84 |

[a]Relative activity is expressed as percentages of the enzyme activity using N-acetyl-D-Met as substrate To determine the optimal reaction pH of NAAAR, N-carbamoyl-D-HPA was dissolved in buffer with different pH values, including: citrate-$Na_2HpO_4$ (pH 2.6~7.6), sodium phosphate buffer (pH 6.0~8.0), Tris-HCl (pH 7.1~8.9) and glycine-NaOH (pH 8.6~10.6). To the substrate solution, 0.5 mM $CoCl_2$ and appropriate amount of the enzyme were added. The reaction mixture was incubated at 50° C. for 30 min, and the reaction was terminated by incubating in boiling water for 5 min. As shown in FIG. 1, preferred reaction buffer for the present NAAAR was Tris-HCl buffer (pH 7.0~9.0).

Figure 2:
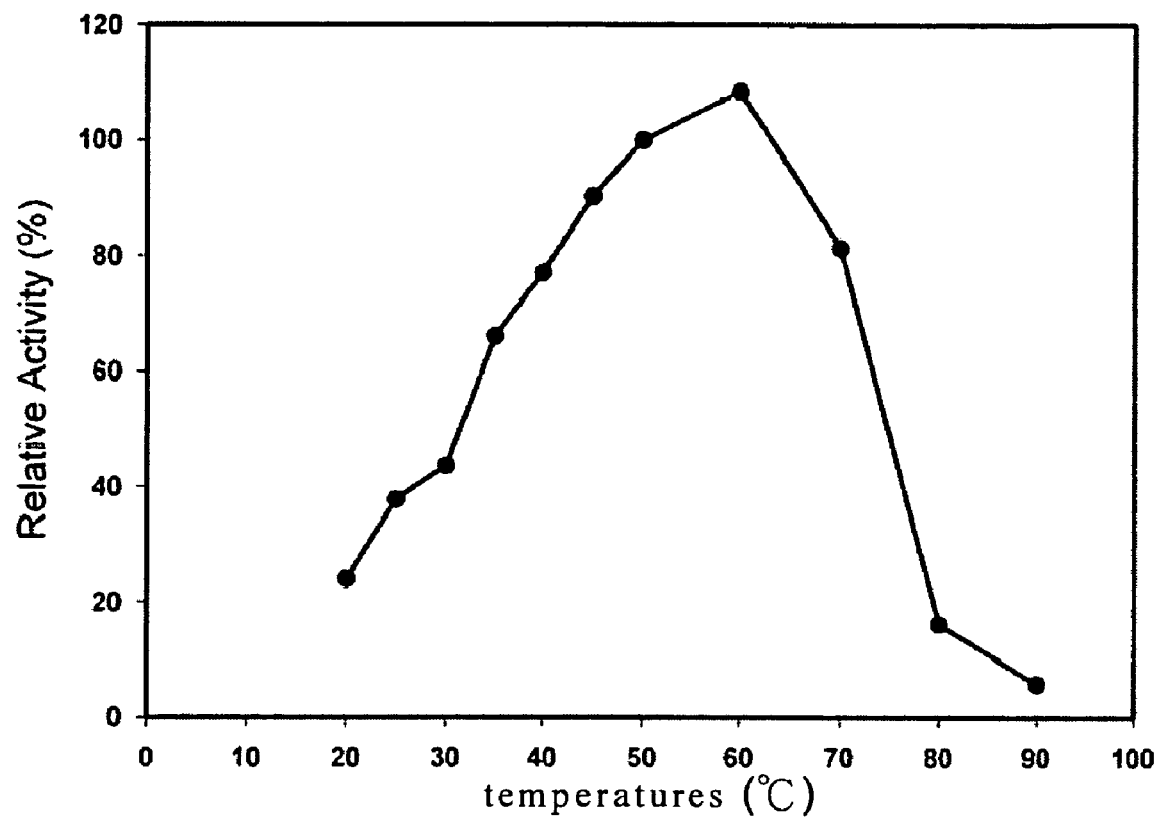
FIG. 2 shows the effects of temperatures on the catalytic activity of the present N-acylamino acid racemase.

To determine the optimal reaction temperature, the reaction mixture containing 50 mM Tris-HCl buffer (pH 8.0), 10 mM substrate N-carbamoyl-D-HPA, 0.5 mM $CoCl_2$ and appropriate amount of the enzyme was incubated at different temperature ranged from 20 to 90° C. for 30 min, and the enzyme activity was measured by the Chiral-HPLC method described above. As shown in FIG. 2, the optimal reaction temperature was 40~70° C.

To determine the effect of metal ion on the enzyme activity, a variety of metal ions at same concentration were added to a solution of the purified NAAAR in 50 mM Tris-HCl buffer (pH 8.0). After incubation at 37° C. stood for 15 min, 10 mM N-carbamoyl-D-HPA was added into the reaction mixture and incubated at 50° C. for 30 min. Enzyme activities were then determined by the Chiral-HPLC method. As shown in Table 2, the present NAAAR exhibited an improved enzymetic activity in the presence of bivalent metal ions such as $Co^{++}$, $Mn^{++}$, and $Ni^{++}$.

TABLE 2

Effects of metal ions on N-acylamino acid racemase activities

| Compounds | Concentration (mM) | Relative activity (%)[a] |
| --- | --- | --- |
| None | 2 | 0 |
| $CaCl_2$ | 2 | 0 |
| $CoCl_2$ | 2 | 100 |
| $CuCl_2$ | 2 | 0 |
| $MnCl_2$ | 2 | 79.1 |
| $MgCl_2$ | 2 | 20.5 |
| $NiCl_2$ | 2 | 40.6 |
| $ZnCl_2$ | 2 | 19.7 |
| EDTA | 10 | 0 |

[a]Relative activity is expressed as percentages of the enzyme activity with $CoCl_2$.

The present NAAAR was analysed its thermostability at 55° C. in the presence of 0.5 mM $CoCl_2$. The half-life of the NAAAR activity was about 15 days, and remained more than 20% of enzymatic activity after 25 days in the reaction condition. Thus, the NAAAR of present invention is considered to be a thermostable enzyme.

Example 2

Conversion of N-Protected HPA to L-HPA by the NAAAR and L-N-Carbamoylase from Transformed *E. coli*

For the co-expression of the NAAAR and L-N-carbamoylase genes in a host cell, we designed two primers at the upstream of T5 promoter and the downstream of λ transcriptional terminator sequence in vector pQE30:

NCAU (5'-ggcgaggatccatgattcaaggggaacgtc-3', SEQ ID NO: 5), containing BamHI restriction site; and NCAD (5'-aatt-taagcttattccccttgggccagttg-3', SEQ ID NO:6), containing HindIII restriction site. The nucleotide sequences encoding the NAAAR and L-N-carbamoylase were amplified from *Deinococcus radiodurans* NCHU1003 and *Bacillus kaustophilus* CCRC11223 chromosome, respectively, by PCR technology. The PCR products contained T5 promoter, lac operator and 6×his-tag sequence at the 5'-end and A transcriptional terminator at the 3'-end. The PCR products were cloned in the pQE30 expression vector. The resultant plasmid, pQEarlnca, was transformed into *E. coli* JM109 for inductive expression.

The reaction mixture containing 10 mM substrate N-carbamoyl-D-HPA, 0.5 mM $CoCl_2$, 50 mM Tris-HCl buffer (pH 8.0), and the enzymes NAAAR and L-N-carbamoylase isolated from induced transformant was incubated at 50° C. for carrying out the conversion. After analysed by the Chiral-HPLC method, it is shown that the co-expressed enzymes could completely convert the original substrate to the final product L-amino acid in 2 to 3 h in one single reaction. The results are shown in the following Table 3.

TABLE 3

Conversion of NCa-D-HPA with enzymes L-N-carbamoylase/ N-acylamino acid racemase

| Time (hour) | NCa-D-HPA (mM) | NCa-L-HPA (mM) | L-HPA (mM) |
| --- | --- | --- | --- |
| 0.5 | 4.16 | 0.88 | 4.96 |
| 1.0 | 1.16 | 0 | 8.84 |
| 2.0 | 0 | 0 | 10 |

Example 3

Conversion of N-Protected HPA to L-HPA by Whole Cell Preparation

The *E. coli* JM109 transfomants harboring co-expression vector, pQEarlnca, were inoculated into 500-mL LB containing 100 ug/ml of ampicillin. The bacteria were cultured at 37° C. until the $OD_{600}$ reach 1. IPTG was added at final concentration of 1 mM to induce the gene expression.

Figure 3:
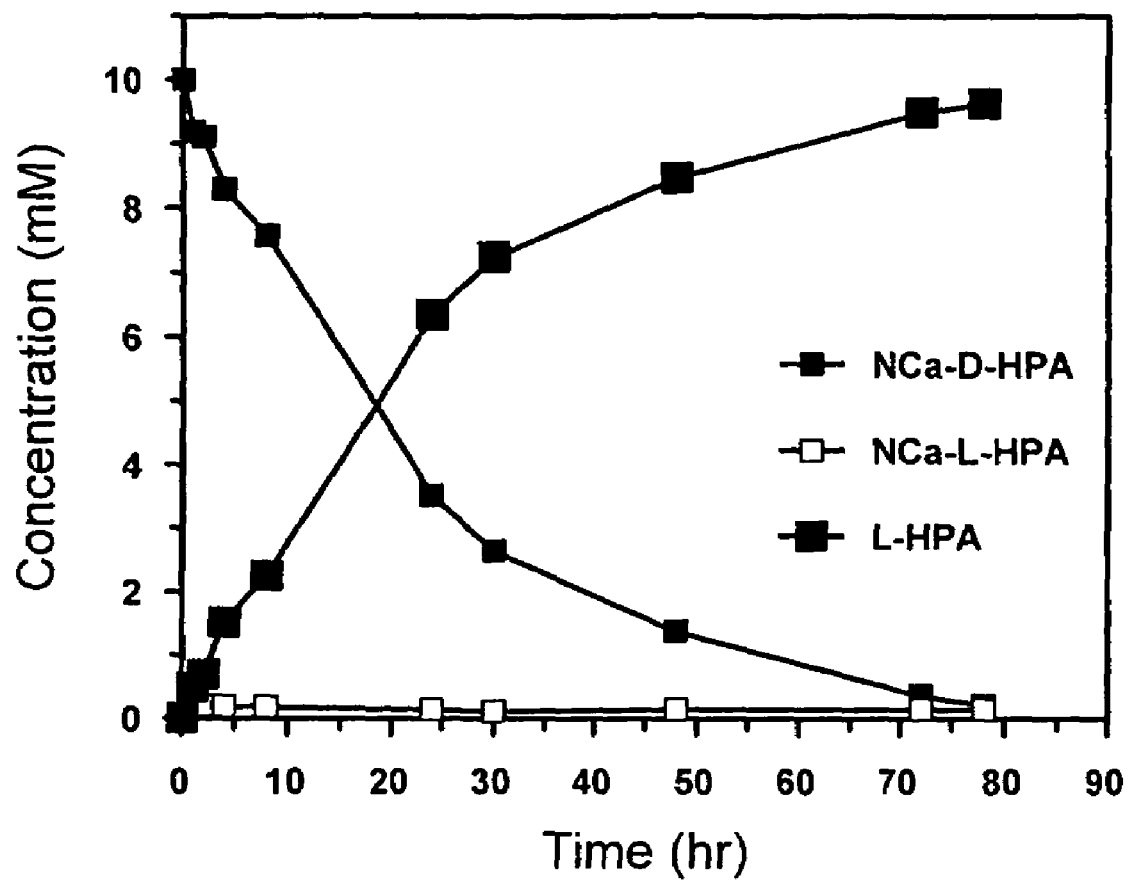
FIG. 3 shows the conversion efficiency of NCa-D-HPA to L-HPA using whole cell preparation of *E. coli* tranformants comprising the nucleotide sequences encoding L-carbamoylase and the present N-acylamino acid racemase, with measuring variations of the substrate NCa-D-HPA, the product L-HPA and the possible byproduct NCa-L-HPA during the conversion reaction.

After the IPTG induction, the bacteria were collected by centrifugation and stored at 4° C. for further usage. In the conversion reaction, 2 g of the wet bacteria preparation was added to 100 ml formulated substrate solution, in which 10 mM N-carbamoyl-D,L-HPA was dissolved in 50 mM Tris-HCl buffer (pH 8.0) containing 0.5 mM $CoCl_2$. The reaction was carried out in a 37° C. water bath with magnetic stirrer, and controlled and maintained the pH value at 7.0 to 8.0 during reaction with 1N HCl and 1N NaOH. Aliquots of 0.5 ml were sampled at intervals for the detection of L-HPA production by the Chiral-HPLC method. After 80 h incubation, the L-HPA conversion yield reached 98%, with an ee value of 99% (FIG. 3).

The strain *E. coli* XLI-Blue containing the recombinant vector pQE-naaar, of the present invention was deposited with the Agricultural Research Service Culture Collection (NRRL), on Nov. 29, 2005, as Deposit No. NRRL-B-30889.

What is claimed is:

1. A process for preparing an optically active L-amino acid from a racemic mixture of an N-protected amino acid, comprising converting N-protected amino acids with a thermostable N-acylamino acid racemase comprising the amino acid sequence of SEQ ID NO:1 combined with L-N-carbamoylase from *Bacillus kaustophilus* to obtain the optically active L-amino acid.

2. The process according to claim 1, wherein the optically active L-amino acid is L-homophenylalanine (L-HPA) and the N-protected amino acid is N-carbamoyl-homophenylalanine.

3. The process of claim 2, wherein the converting reaction is carried out in the presence of a bivalent metal ion.

4. The process of claim 2, wherein the bivalent metal ion is $Co^{++}$, $Mn^{++}$, or $Ni^{++}$.

5. The process of claim 2, wherein the N-acylamino acid racemase and the L-N-carbamoylase are co-expressed in a host cell transformed with a vector comprising the N-acylamino acid racemase and L-N-carbamoylase coding sequences.

6. The process of claim 2, wherein the *Bacillus kaustophilus* is *Bacillus kaustophilus* CCRC 11223.

7. The process according to claim 1, wherein the N-protected amino acid is selected from the group consisting of N-acetyl-HPA, N-acetyl-Phe, N-acetyl-Met, N-acetyl-Phe, N-acetyl-Gln, N-acetyl-Leu, N-acetyl-Trp, N-carbamoyl-homophenylalanine, and N-chloroacetyl-Phe.

8. A process for preparing L-homophenylalanine (L-HPA), comprising converting N-carbamoyl-HPA with a thermostable N-acylamino acid racemase combined with L-N-carbamoylase from a *Bacillus* sp. at 20~80° C. in Tris-HCl buffer (pH 5.0~10.0) to obtain optically active L-HPA, and wherein said thermostable N-acylamino acid racemase is isolated from *Deinococcus radiodurans* NCHU1003, which converts N-protected amino acids to corresponding L-amino acids when combined with L-N-carbamoylase and comprises the amino acid sequence of SEQ ID NO:1.

9. The process of claim 8, further comprising:
(A) transforming host cells with a recombinant vector comprising a DNA molecule encoding said N-acylamino acid racemase and regulatory elements;
(B) culturing the transformants under a condition sufficient for expression of said N-acylamino acid racemase; and
(C) recovering and/or purify the N-acylamino acid racemase.

10. The process of claim 8, in which the converting reaction is carried out in the presence of a bivalent metal ion.

11. The process of claim 10, in which the bivalent metal ion is $Co^{++}$, $Mn^{++}$, or $Ni^{++}$.

12. The process of claim 8, in which the N-acylamino acid racemase and/or the L-N-carbamoylase are immobilized on a support.

13. The process of claim 8, in which the N-acylamino acid racemase and the L-N-carbamoylase are co-expressed in a host cell transformed with a vector comprising the N-acylamino acid racemase and L-N-carbamoylase coding sequences.

14. The process of claim 13, in which the converting reaction is carried out in a whole cell preparation.

15. A process for preparing L-homophenylalanine (L-HPA), comprising converting N-carbamoyl-HPA with a thermostable N-acylamino acid racemase combined with L-N-carbamoylase from *Bacillus kaustophilus* at 20~80° C. in Tris-HCl buffer (pH 5.0~10.0) to obtain optically active L-HPA, and wherein said thermostable N-acylamino acid racemase comprises the amino acid sequence of SEQ ID NO:1.

16. The process of claim 15, wherein the converting reaction is carried out in the presence of a bivalent metal ion.

17. The process of claim 16, wherein the bivalent metal ion is $Co^{++}$, $Mn^{++}$, or $Ni^{++}$.

18. The process of claim 15, wherein the N-acylamino acid racemase and/or the L-N-carbamoylase are immobilized on a support.

19. The process of claim 15, wherein the N-acylamino acid racemase and the L-N-carbamoylase are co-expressed in a host cell transformed with a vector comprising the N-acylamino acid racemase and L-N-carbamoylase coding sequences.

20. The process of claim 19, wherein the converting reaction is carried out in a whole cell preparation.

* * * * *

UNITED STATES PATENT AND TRADEMARK OFFICE
CERTIFICATE OF CORRECTION

PATENT NO. : 7,629,154 B2 Page 1 of 1
APPLICATION NO. : 11/316818
DATED : December 8, 2009
INVENTOR(S) : Hsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 260 days.

Signed and Sealed this

Twenty-first Day of December, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 375
<212> TYPE: PRT
<213> ORGANISM: Deinococcus radiodurans

<400> SEQUENCE: 1

```
Met Ala His Thr Gly Arg Met Phe Lys Ile Glu Ala Ala Glu Ile Val
1               5                   10                  15

Val Ala Arg Leu Pro Leu Lys Phe Arg Phe Glu Thr Ser Phe Gly Val
            20                  25                  30

Gln Thr His Lys Val Val Pro Leu Leu Ile Leu His Gly Glu Gly Val
        35                  40                  45

Gln Gly Val Ala Glu Gly Thr Met Glu Ala Arg Pro Met Tyr Arg Glu
    50                  55                  60

Glu Thr Ile Ala Gly Ala Leu Asp Leu Leu Arg Gly Thr Phe Leu Pro
65                  70                  75                  80

Ala Ile Leu Gly Gln Thr Phe Ala Asn Pro Glu Ala Val Ser Asp Ala
                85                  90                  95

Leu Gly Ser Tyr Arg Gly Asn Arg Met Ala Arg Ala Met Val Glu Met
            100                 105                 110

Ala Ala Trp Asp Leu Trp Ala Arg Thr Leu Gly Val Pro Leu Gly Thr
        115                 120                 125

Leu Leu Gly Gly His Lys Glu Gln Val Glu Val Gly Val Ser Leu Gly
    130                 135                 140

Ile Gln Ala Asp Glu Gln Ala Thr Val Asp Leu Val Arg Arg His Val
145                 150                 155                 160

Glu Gln Gly Tyr Arg Arg Ile Lys Leu Lys Ile Lys Pro Gly Trp Asp
                165                 170                 175
```

```
Val Gln Pro Val Arg Ala Thr Arg Glu Ala Phe Pro Asp Ile Arg Leu
            180                 185                 190

Thr Val Asp Ala Asn Ser Ala Tyr Thr Leu Ala Asp Ala Gly Arg Leu
            195                 200                 205

Arg Gln Leu Asp Glu Tyr Asp Leu Thr Tyr Ile Glu Gln Pro Leu Ala
            210                 215                 220

Trp Asp Leu Val Asp His Ala Glu Leu Ala Arg Arg Ile Arg Thr
225                 230                 235                 240

Pro Leu Cys Leu Asp Glu Ser Val Ala Ser Ala Ser Asp Ala Arg Lys
            245                 250                 255

Ala Leu Ala Leu Gly Ala Gly Val Ile Asn Leu Lys Val Ala Arg
            260                 265                 270

Val Gly Gly His Ala Glu Ser Arg Val His Asp Val Ala Gln Ser
            275                 280                 285

Phe Gly Ala Pro Val Trp Cys Gly Gly Met Leu Glu Ser Gly Ile Gly
            290                 295                 300

Arg Ala His Asn Ile His Leu Ser Thr Leu Ser Asn Phe Arg Leu Pro
305                 310                 315                 320

Gly Asp Thr Ser Ser Ala Ser Arg Tyr Trp Glu Arg Asp Leu Ile Gln
            325                 330                 335

Glu Pro Leu Glu Ala Val Asp Gly Leu Met Pro Val Pro Gln Gly Pro
            340                 345                 350

Gly Thr Gly Val Thr Leu Asp Arg Glu Phe Leu Ala Thr Val Thr Glu
            355                 360                 365

Ala Gln Glu Glu His Arg Ala
            370                 375

<210> SEQ ID NO 2
<211> LENGTH: 1128
<212> TYPE: DNA
<213> ORGANISM: Deinococcus radiodurans

<400> SEQUENCE: 2
atggcgcata ctggccgtat gttcaaaatc gaagctgctg aaatcgtcgt ggcgcggctg      60
ccgctcaagt tccgctttga acgagtttc ggggtgcaga cccacaaggt ggtgccgctg     120
ctcattctcc acggcgaagg cgtgcagggc gtcgccgagg caccatgga agcgcggccc     180 atgtaccgcg aggaaacgat tgccggggca ctggacctgc tgcgcggcac cttttttgccc     240 gccatcctgg ggcagaccct tcgccaaccc gaagcggtga gcgacgcact cggcagctac     300
aggggcaacc gcatggcgcg ggcgatggtg gaaatggcgg cctgggacct ctgggcgcgc     360
acgctggggg tgccgctcgg aacactactc ggcggtcaca aggagcaggt ggaggtgggg     420
gtcagcctcg gcattcaggc ggacgagcag gcgacggtgg acctcgtgcg ccggcatgtc     480
gagcagggct accgccgtat caaactcaag atcaaaccg ctgggacgt gcagccggta     540 cgcgcgaccc gcgaggcctt tcccgacatt cgcctgacgg tggacgccaa cagcgcctac     600
accctggccg acgccgggcg gctgcggcaa ctcgacgagt acgacctgac ctacatcgag     660
cagccgctcg cctgggacga cctcgtggac cacgctgaac tcgcccggcg cattcgcacg     720
ccgctgtgcc tcgacgagtc ggtggcgtcg gcgtcgacg cccgcaaggc gctggcgctg     780
ggcgcgggcg gcgtcatcaa cctcaaggtg gcccgcgtgg gcggacacgc cgagtcgcgg     840
cgcgtgcacg acgtggccca gagcttcggc gccccggtgt ggtgcggcgg gatgctggag     900
agcggcatcg gcgggcgcca caacatccac ctctcgacgc tgtccaactt ccgcttgccg     960
```

```
ggcgacacca gttcggccag ccgctactgg gagcgcgacc tgattcagga accgctcgaa    1020
gcggtggacg gcttgatgcc ggtgccgcag gggccgggca caggcgtaac ccttgaccgc    1080
gagttcctgg cgaccgtcac cgaggcgcag gaggaacacc gggcgtga                1128
```